United States Patent [19]

Abe et al.

[11] Patent Number: 4,742,713

[45] Date of Patent: May 10, 1988

[54] ULTRASONIC FLAW DETECTING SYSTEM

[75] Inventors: Akira Abe, Osaka; Isamu Ishida, Tokyo; Kaneyoshi Katsumata, Yamato, all of Japan

[73] Assignee: Omron Tateisi Electronics Co., Kyoto, Japan

[21] Appl. No.: 21,576

[22] Filed: Mar. 2, 1987

Related U.S. Application Data

[63] Continuation of Ser. No. 740,488, Jun. 3, 1985, abandoned.

[30] Foreign Application Priority Data

Jun. 1, 1984 [JP] Japan ............................ 59-112554
Jun. 1, 1984 [JP] Japan ............................ 59-112555
Jun. 7, 1984 [JP] Japan ............................ 59-118671
Jun. 13, 1984 [JP] Japan ............................ 59-121033
Jun. 18, 1984 [JP] Japan ............................ 59-124819
Jun. 18, 1984 [JP] Japan ............................ 59-124820

[51] Int. Cl.$^4$ ............................................ G01N 29/00
[52] U.S. Cl. ........................................ 73/620; 73/618
[58] Field of Search ............... 73/620, 618, 621, 627, 73/629, 633; 364/507

[56] References Cited

U.S. PATENT DOCUMENTS 3,178,933  4/1965  Bloch et al. ........................... 73/620
3,534,590 10/1970  Kent et al. ............................ 73/618
4,170,145 10/1979  Kennedy et al. ..................... 73/620

Primary Examiner—Michael J. Tokar
Assistant Examiner—Louis M. Arana
Attorney, Agent, or Firm—Foley & Lardner, Schwartz, Jeffery, Schwaab, Mack, Blumenthal & Evans

[57] ABSTRACT

An ultrasonic flaw detecting system comprises a manual scanning unit equipped with a probe and capable of producing a probe position data signal, an ultrasonic flaw detector for transmitting an ultrasonic signal to the probe and producing flaw detection data on the basis of a reflection echo signal as received, and a data collecting/recording unit for receiving the flaw detection data from the ultrasonic flaw detector and the probe position data from the manual scanning unit to record both data on an external recording medium, wherein the scanning unit, the ultrasonic flaw detector and the data collecting/recording unit constitute a portable flaw detection data collecting apparatus. The data stored on the external recording medium can be loaded in a data processing apparatus installed at a predetermined location independent of the portable flaw detection data collecting apparatus to be thereby automatically processed for obtaining various information of flaw possibly present within an object to be tested. Due to the provision of the manually manipulatable scanning unit, the scanning operation for searching flaws can be effected in a flexible manner when compared with the conventional autonatic scanning unit, whereby flaw detection can be accomplished with an improved accuracy and high reliability.

8 Claims, 14 Drawing Sheets

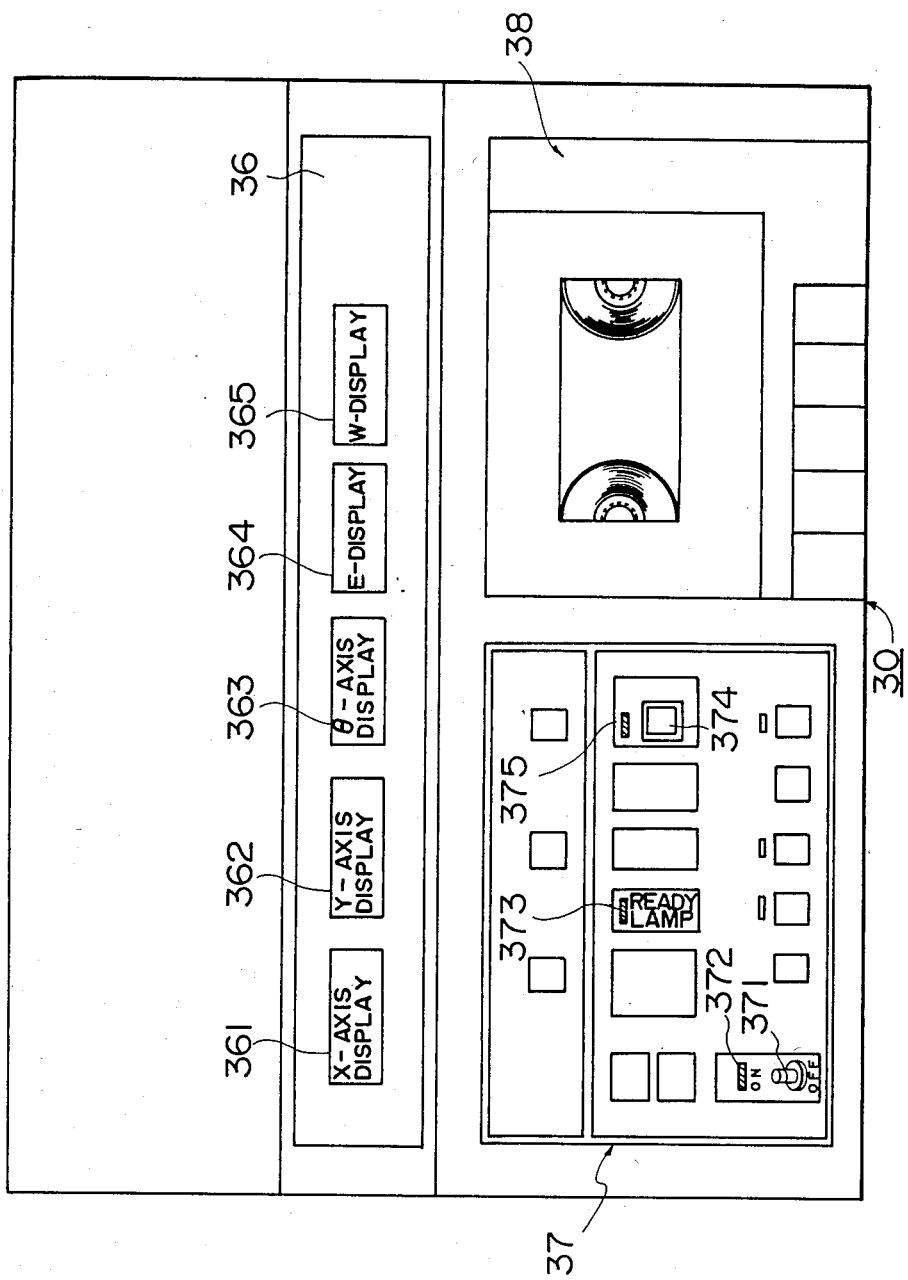

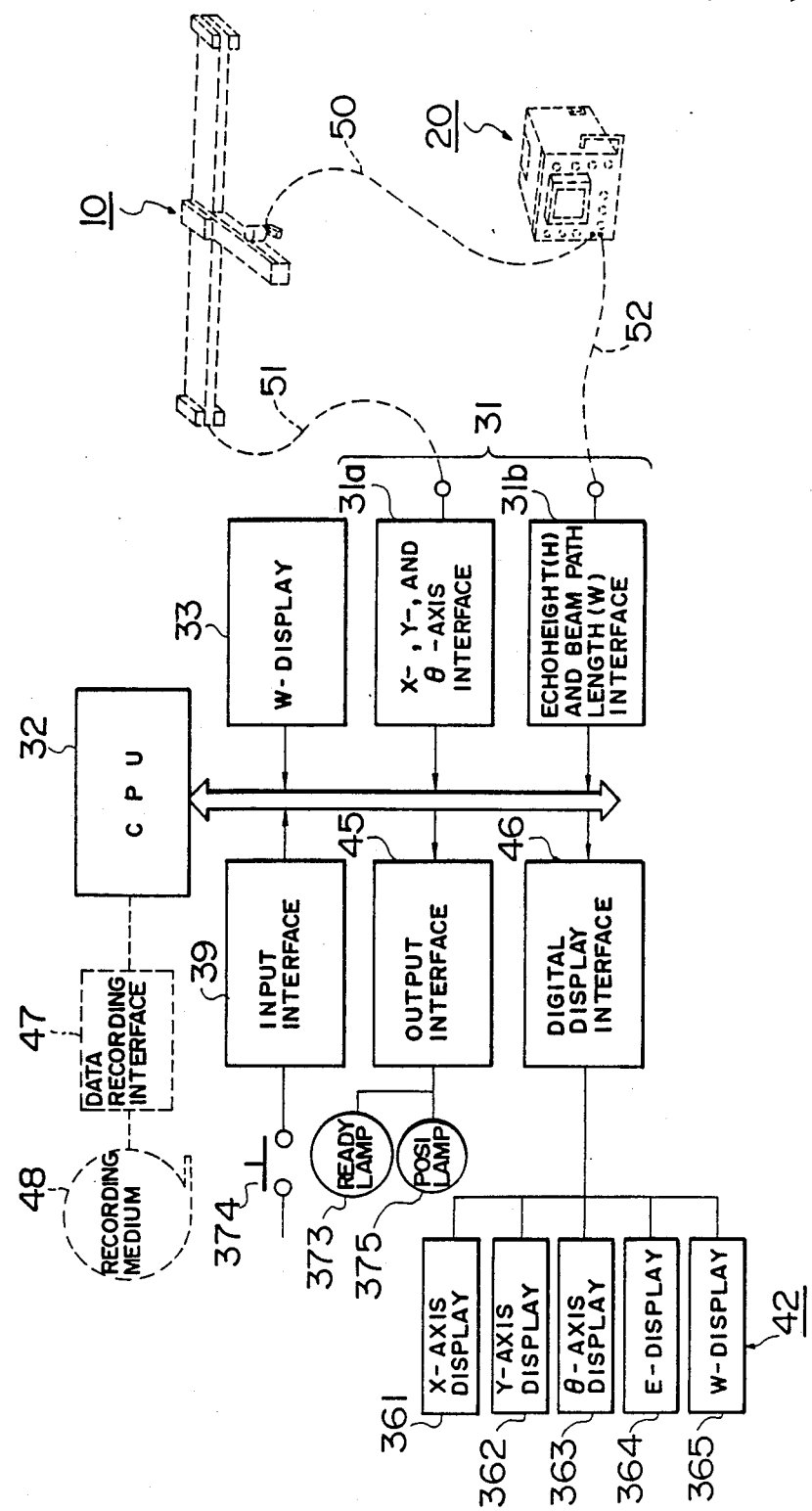

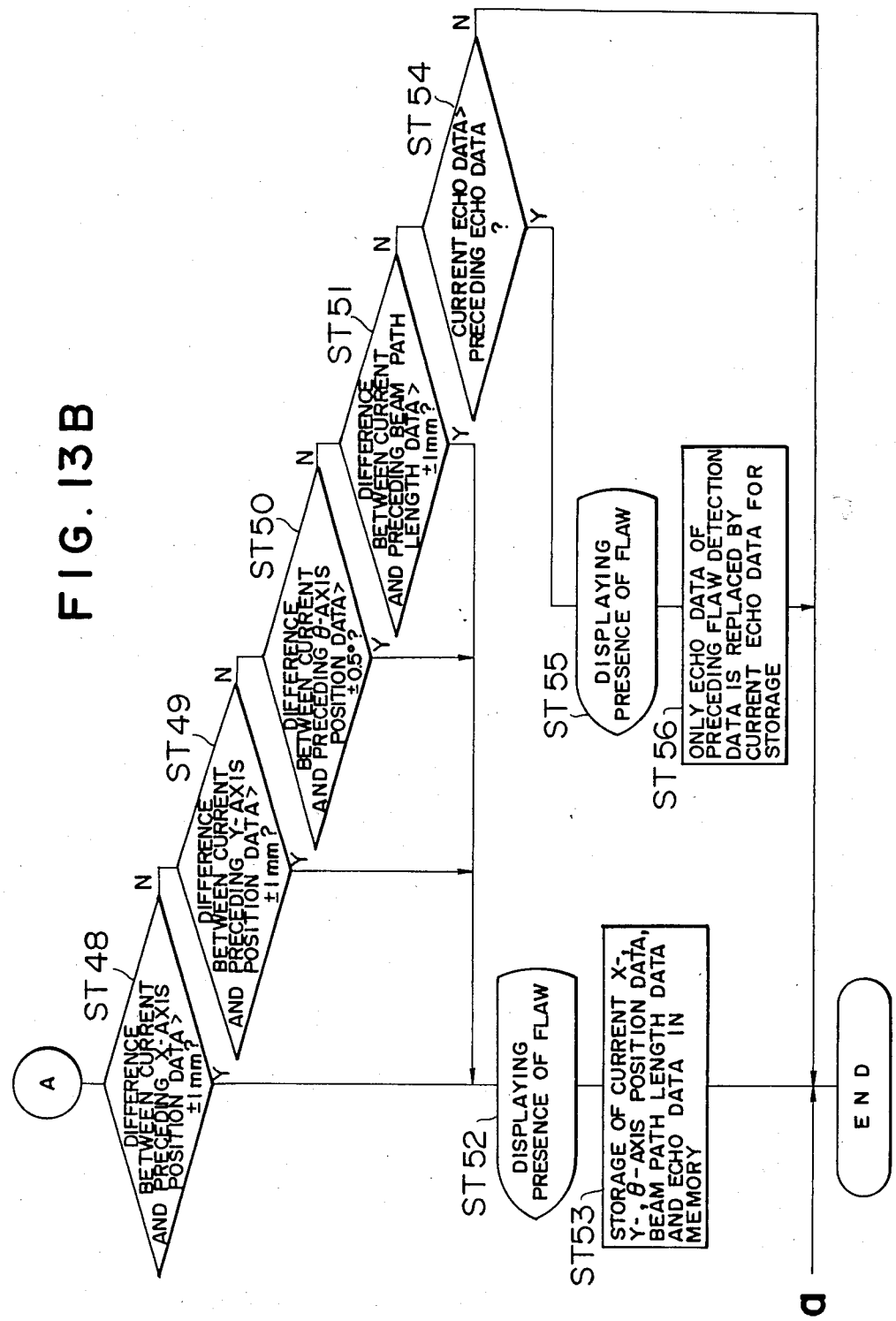

FIG. 14
FIG. 15
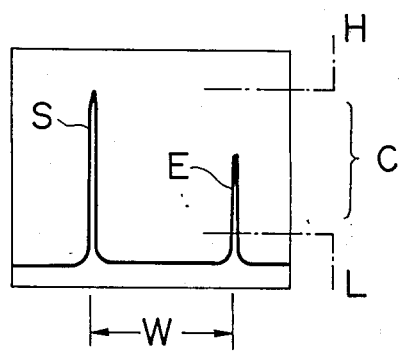
FIG. 16
(a)                    (b)
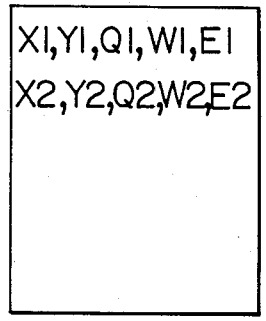 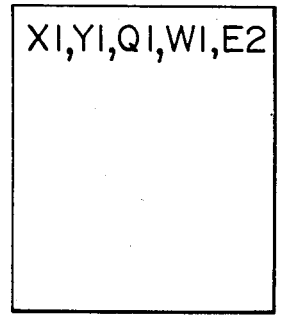

ULTRASONIC FLAW DETECTING SYSTEM

This application is a continuation of application Ser. No. 740,488, filed June 3, 1985, now abandoned.

FIELD OF THE INVENTION

The present invention relates generally to an ultrasonic flaw detecting system and more particularly to a type of ultrasonic flaw detecting system in which a probe is manually manipulated for the scanning operation, wherein all of the flaw data resulting from the scanning operation is automatically collected and recorded at the location of the flaw detection and processed by a data processing unit installed independently at a remote location.

DESCRIPTION OF THE PRIOR ART

Heretofore, a so-called automatic ultrasonic flaw detecting system has been known in which a probe adapted to transmit an ultrasonic wave to a material to be examined or tested and to receive an echo therefrom is caused to automatically scan the material under test to thereby detect lack of fusion, cracks, cavities or holes or foreign materials possibly present within the material under test, and at the same time the flaw data thus obtained is automatically recorded for subsequent analyses and processing for analysis and identification of the flaws which are automatically carried out. The automatic flaw detecting system of this type is advantageous in that man-power can be reduced, the recording can be automatically effected and error due to difference in skill among individual operators can be avoided. However, the hitherto known system suffers various shortcomings. First, difficulty is encountered in scanning the material under test with the probe in a rather complicated manner. For example, it is practically impossible to scan the same portion of the material repetitively with the probe to confirm the result of the flaw detection, as occasion requires. As a concequence, the reliability of the automatic flaw detection is low as compared with the manual flaw detection (i.e. flaw detection performed through manual scanning). In the hitherto known system of this type, an automatic sequence control with the aid of a computer is adopted, as the result of which a power supply unit of a large size is required, whereby the bulk of the apparatus as a whole is increased to make it difficult or impracticable to transport the apparatus to the place where the flaw detection is to be carried out. Further, apart from the expense of the equipment, the detection speed control can not be accomplished in such a manner in which the portion of the material under test where the flaw echo, ghost echo or the like is detected is carefully examined for discriminating the valid flaw signal from noise while those locations where no reaction is detected are examined at a high speed, because the scanning is effected at a constant speed in the hitherto known system. Consequently, the recording of flaw data is less effective when compared with the manual flaw detection. Additionally, because the pressing force applied to the probe is constant, the latter can not follow with fidelity the non-uniform surface of the material under test, involving loss of valid flaw data and thus rendering it impossible to record the detected flaw data with requisite reliability and accuracy.

SUMMARY OF THE INVENTION

A first object of the present invention to provide an inexpensive ultrasonic flaw detection data collecting-/recording apparatus in which a manual scanning with a probe is adopted for flaw detection, wherein the whole apparatus can be easily transported to a place where the flaw detection is to be carried out and all of the raw data as obtained can be collected and recorded in situ on an external storage medium such as cassette tape, floppy disc or the like.

A second object of the present invention is to provide an ultrasonic flaw detecting system in which the raw data resulting from the in-situ flaw detection can be loaded into a data processing apparatus provided separately and independent of other units for performing high speed processing of the flaw detection data to assure the flaw detection with an improved reliability, and which system enjoys advantages of both hitherto known automatic ultrasonic wave flaw detecting apparatus and manual flaw detecting apparatus.

In view of the above objects, the present invention resides in an ultrasonic flaw detecting system which comprises a manual scanning unit equipped with a probe adapted to be mounted detachably on a material to be tested and capable of outputting probe position data, an ultrasonic flaw detector capable of transmitting an ultrasonic wave to the probe of the manual scanning unit and outputting flaw detection data on the basis of a reflection or echo signal produced by the probe, a data recording unit for receiving data of the flaw detection from the ultrasonic flaw detector as well as the probe position data from the manual scanning unit to record both data on an external storage medium, said manual scanning unit, ultrasonic flaw detector and data recording unit cooperating to constitute a portable flaw detection data collecting/recording apparatus, and a data processing apparatus installed at a remote location separately and independently from the aforementioned composite units for processing the data recorded on the external storage medium.

With the phrase "probe position data", it is intended to cover all the data of displacemment of the probe along the X-axis, displacement along the Y-axis and probe's rotational angle about the $\theta$-axis, while the phase "flaw detection data" is used in the sense to encompass data of the beam path length and magnitude of echo also referred to as echo height. As the external recording medium, a cassette tape, a floppy-disc or the like is preferred.

With the arrangement of the ultrasonic flaw detection data collecting/recording apparatus described above, the scanning operation can be carried out with the probe being in intimate contact with the surface of a material under test notwithstanding unevenness of the surface thereof. As a result, undesirable loss of the flaw detection data which the hitherto known system suffers can be excluded, which in turn means that the flaw detection data can be obtained with an improved reliability. The flaw detection data can be collected and recorded for preservation as the raw information. Additionally, since the speed at which the flaw detection is carried out can be controlled in an arbitrary manner, it is possible to effect the high speed scanning operation at the location where no flaw is detected while the scanning is performed carefully at a low speed at locations where flaw is detected, by visually observing information displayed on a CRT (chathode ray tube) display unit. Consequently, the flaw data can be collected and recorded with an improved accuracy through the effective flaw detecting operation. Further, in contrast to the hitherto known automatic scanning apparatus of complicated and expensive structure, the manual scanning unit or scanner according to the invention is realized in a much simplified structure in consideration of the convenience of portability. Accordingly, the cost of the whole system according to the invention can be significantly reduced. In other words, there is provided an inexpensive system according to the invention.

The other objects and advantages of the invention will be apparent from the following detailed description taken in conjunction with the drawings.

BRIEF DESCRIPTION OF THE DRAWINGS

FIG. 11 is a front view showing schematically a configuration of a data collecting/recording unit employed in the ultrasonic flaw detecting system according to the present invention.

FIG. 12 is a block diagram showing schematically a general arrangement of the data collecting/recording unit shown in FIG. 11.

FIGS. 13A and 13B is a flow chart for illustrating operation of fetching flaw detection data performed by the data collecting/recording unit shown in FIGS. 11 and 12.

FIG. 14 is a timing chart for illustrating sampling timing or sampling time points in the flaw data fetching operation.

FIG. 15 is a waveform diagram for illustrating a predetermined reference range in the flaw data fetching operation.

FIG. 16(a) is a view for illustrating the state in which data resulted from the current and preceding flaw detections are separately stored in a flaw detection data storing memory.

FIG. 16(b) is a view for illustrating the state of the flaw detection data storing memory in which the preceding flaw detection data is partially replaced by the data obtained from the current flaw detection.

DESCRIPTION OF THE PREFERRED EMBODIMENTS

In the following, the present invention will be described in more detail in conjunction with the exemplary embodiments thereof.

Figure 1:
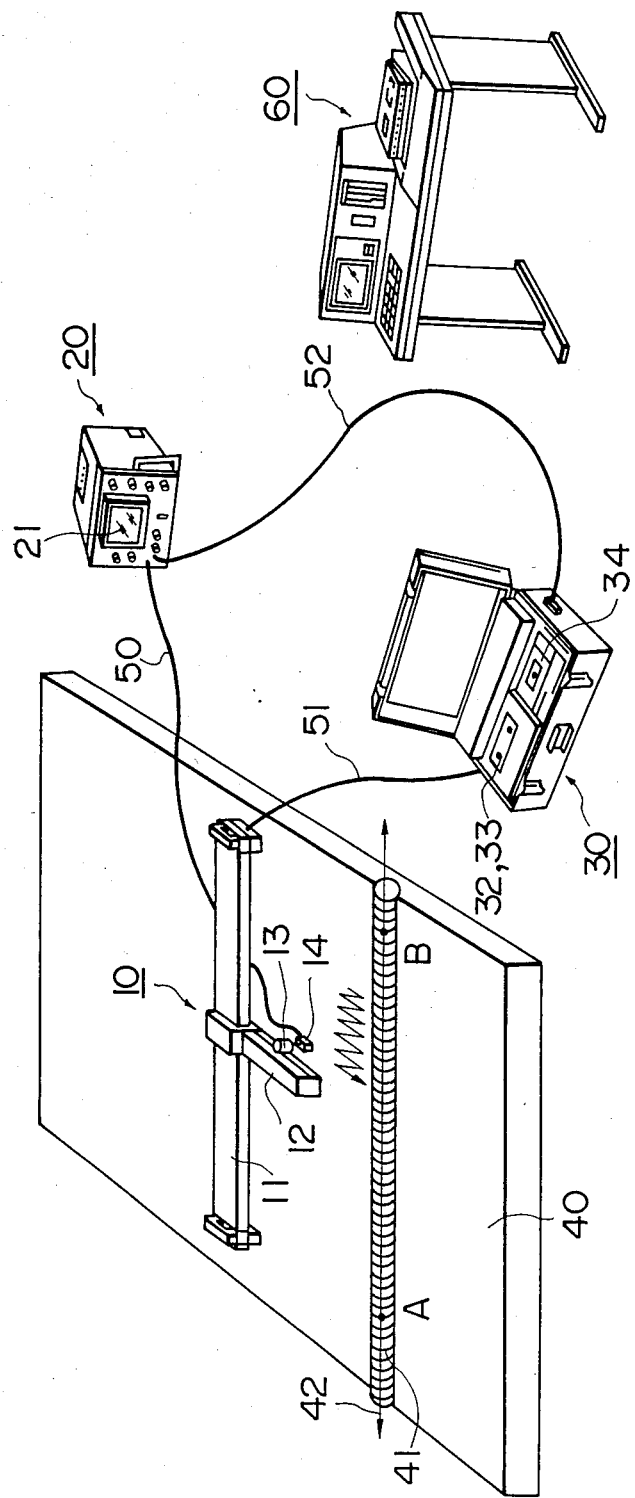
FIG. 1 is a pictorial view illustrating a general arrangement of an ultrasonic flaw detecting system according to an exemplary embodiment of the invention.
Figure 2:
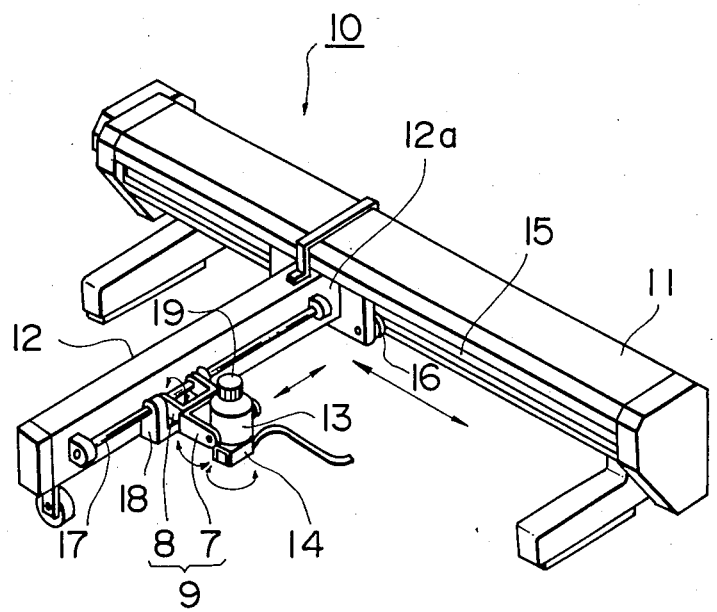
FIG. 2 is a perspective view showing an outer appearance of a scanning unit employed in the ultrasonic flaw detecting system according to the present invention.
Figure 3:
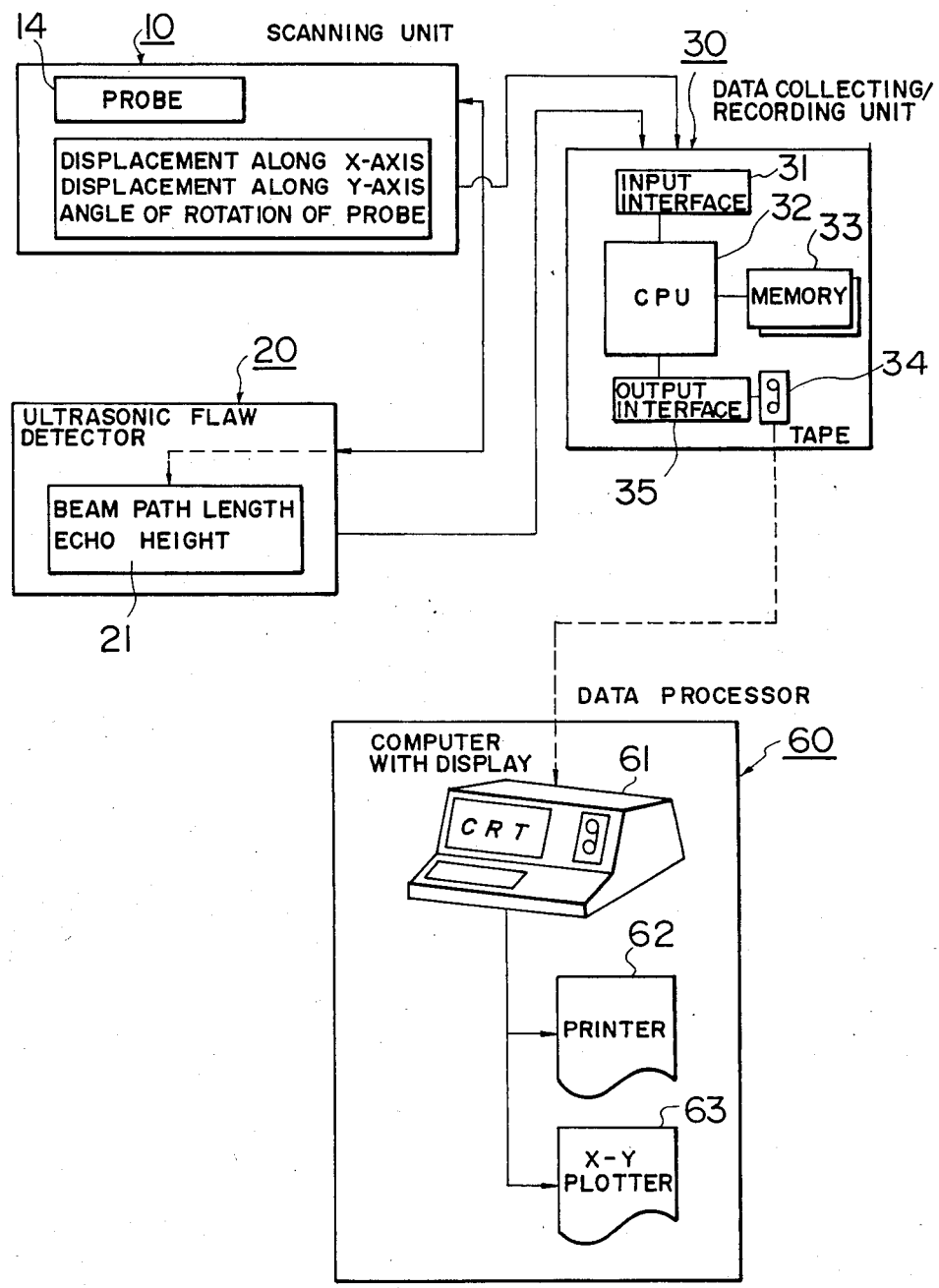
FIG. 3 is a block diagram showing an arrangement of data collecting/recording apparatus used in the ultrasonic flaw detecting system according to the invention.

FIG. 1 is a pictorial view showing the ultrasonic flaw detecting system as a whole according to an exemplary embodiment, FIG. 2 is a view showing a general arrangement of a scanning unit employed in the ultrasonic flaw detecting system according to the invention, and FIG. 3 is a block diagram showing an arrangement of data collecting/recording apparatus employed in the ultrasonic flaw detecting system according to the present invention.

In FIGS. 1 and 2, a reference numeral 10 denotes a manual scanning unit, 20 denotes an ultrasonic flaw detector, 30 denotes a data collecting/recording unit, 60 denotes a data processing apparatus, 40 denotes a material to be examined which is constituted by a pair of metal plates joined together by welding, and 41 denotes a weld seam. The ultrasonic flaw detector 20 and the data collecting/recording unit 30 may be combined together in an integral structure.

The scanning unit 10 is composed of an X-axis member 11 which is adapted to be placed on the material 40 under test by a suitable means such as a magnet, a Y-axis member 12 adapted to be slideably guided by and along the X-axis member 11, and an $\theta$-axis member 13 mounted rotatably on the Y-axis member 12 at a free end portion thereof and adapted to hold the probe 14 at the bottom end thereof. More particularly, referring to FIG. 2, the X-axis member 11 of the scanning unit 10 is disposed in parallel with the weld line 42 on the material 40 under test and provided with a longitudinal guide rail 15, wherein the Y-axis member 12 is connected to the X-axis member 11 orthogonally thereto and supported slideably along the rail 15. To this end, the Y-axis arm member 12 has a base portion 12a provided with rollers 16 which engage the guide rail 15, so that the Y-axis arm member 12 can easily move to the left or to the right, as viewed in FIGS. 1 and 2. The Y-axis arm member 12 is further provided with a guide member 17 of a rod-like configuration which extends in parallel with the Y-axis arm member 12. A carriage 18 slideably mounted on the guide rod 17 supports universally rotatably the probe holder 13 by means of a supporting mechanism generally denoted by a numeral 9. More specifically, the supporting mechanism 9 is composed of a fork member 7 serving to support the probe holder 13 swingably relative to the plane of the material 40 under test. On the other hand, the fork-like holder member 7 is pivotally connected to a fork-like link member 8 which in turn is rotatably and slideably mounted on the aforementioned guide rod 17. In this manner, the probe holder 13 can be moved universally in both vertical and horizontal directions. Mounted detachably on the holder 13 is the aforementioned probe 14 which is rotatable around the longitudinal axis of the holder 13 by means of scanning knob 19.

With the structure of the scanning unit 10, described above, the scanning of the material 40 under test in the longitudinal and transversal directions as well as rotational scan, pendulum-like scan, zig-zag scan and the parallel scan either in upstanding or inclined position can be carried out, wherein the position data such as the position of the Y-axis arm member 12 movable relative to the X-axis base member 11, the position of the probe 14 movable relative to the Y-axis arm member 12 and the rotational or swing angle $\theta$ of the probe 14 as well as the flaw detection data of beam path distance or length W at a flaw-detected position and magnitude of the echo (referred to as the echo height) E are produced and supplied to the data collecting/recording unit 30. The probe 14 is adapted to be electrically energized by an ultrasonic flaw detector 20 by way of a transmission cable 50 to thereby emit an ultrasonic beam toward the interior of the material 40 under test, e.g. at the weld seam 41 and receive the so-called reflection echo inclusive of the flaw echo produced upon reflection of the ultrasonic beam at a crack, bubble or the like possibly present internally of the weld 14 or ghost echo which appears as if it were a flaw echo. Further, the manual scanning unit 10 is imparted with means for transmitting the positional data of the probe 14 such as data of displacements of the probe relative to the X-axis base member 11 and the Y-axis arm member 12 and the rotational or swing angle of the probe holder 13 to the data collecting/recording unit 30 though a transmission cable 51.

The ultrasonic flaw detector 20 includes a high-frequency pulse generating oscillator, an attenuator, a detecting amplifier and others (all not shown) for transmitting ultrasonic energy to the probe 14 through the cable 50 in addition to the CRT display 21. Further, the ultrasonic flaw detector 20 incorporates therein the function unit for analyzing the detected flaw on the basis of the received reflection echo, more particularly, the flaw echo, wherein the results of the analysis are displayed on the CRT while the flaw detection data including the beam path length and the magnitude of echo or echo height are supplied to the data collecting-/recording unit 30 through the cable 52.

Referring to FIG. 3, the data collecting/recording unit 30 includes in general an input interface 31 for receiving the probe position data including the rotational angle of the $\theta$-axes and the displacements of the probe along the X- and Y-axis as supplied from the scanning unit 10 through the transmission cable 51 and the flaw detection data supplied from the ultrasonic flaw detector 20, a central processing unit or CPU 32 for processing both of these data, an internal storage unit or memory 33 for storing the data, and a output interface 35 equipped with transfer port for transferring the data supplied from the CPU 32 and/or the memory 33 to an external recording or storing medium 34 such as cassette tape, floppy disc or the like.

The data processing apparatus 60 is adapted to process the collected data stored in the external recording medium 34 of the data collecting/recording unit 30 and performs classification or graduation of flaws in accordance with predetermined standards (such as JIS standards, ASA standards or the like). The data processing unit 60 is spatially separated from the aforementioned scanning unit 10, the ultrasonic flaw detector 20 and the data collecting/recording unit 30 and may be installed, for example, at a central control station. The data processing apparatus 60 includes a micro-computer 61 provided with a CRT display, a printer 62 for printing out requisite data, and an X-Y plotter 63 for plotting cross-sectional profiles (longitudinal and transversal sectional profiles) as well as a plan profile or pattern of a flaw.

Figure 4:
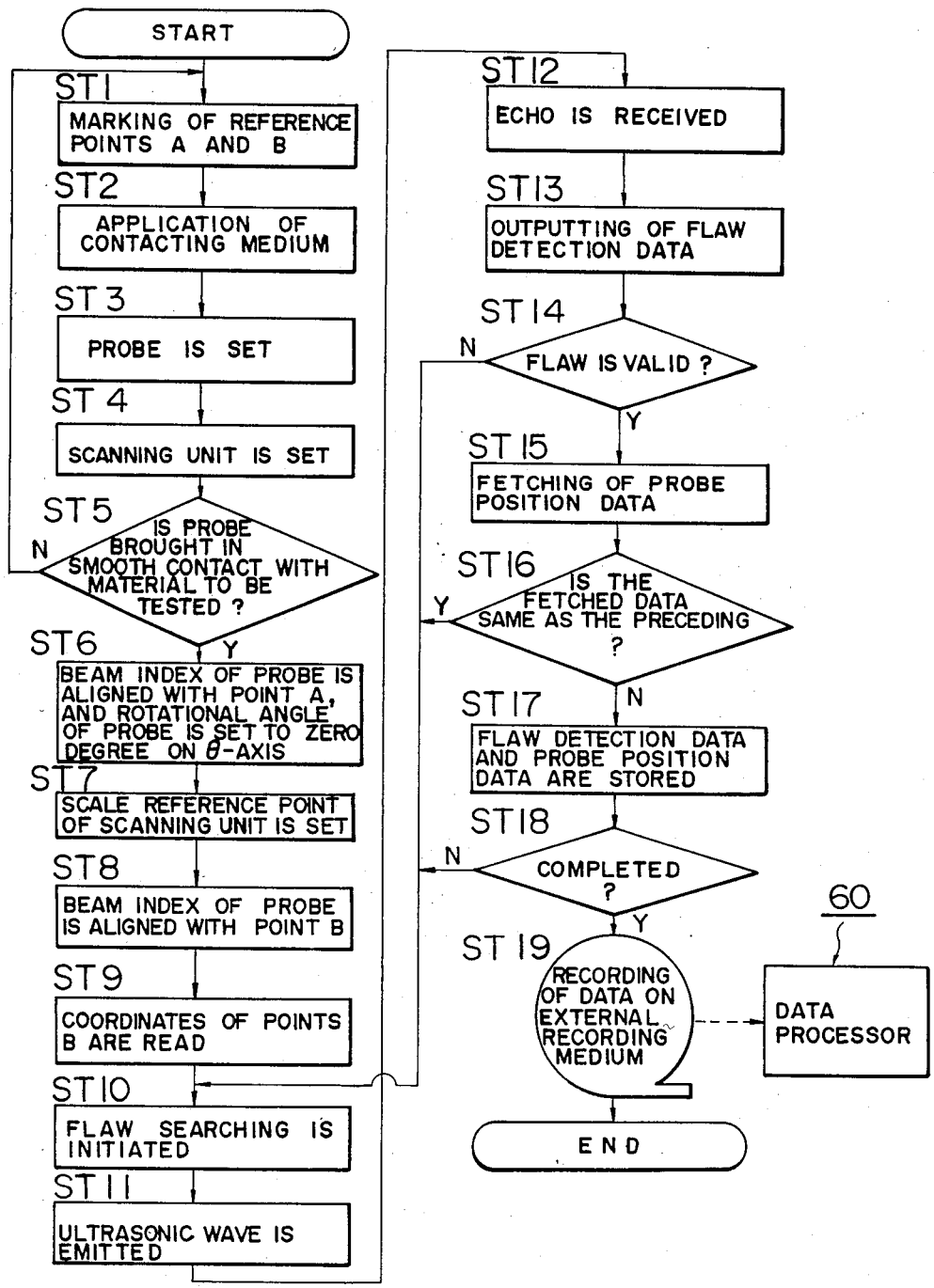
FIG. 4 is a flow chart for illustrating operations of the ultrasonic flaw detecting system.

Next, operation of the ultrasonic flaw detection system described above in conjunction with FIGS. 1 to 3 will be elucidated by referring to the flow chart shown in FIG. 4.

After turning-on of the power supply source of the system, reference points A and B are marked on a weld line 42 of the material 40 under test with an appropriate distance between the points A and B, as is shown in FIG. 1 (step 1 or ST 1). Subsequently, a contacting medium such as oil, water, glycerol or the like is applied over the surface of the material 40 at locations where the flaw detection is to be effected so that no air gap is produced between the probe 14 and the surface to be scanned (step 2 or ST 2). The probe 14 is then mounted on the scanning unit 10 (step 3), which in turn is positioned on the material 40 under test (step 4). Subsequently, it is checked whether the probe 14 can smoothly contact the material 40 under test (step 5). Unless smooth contact is attained, the aforementioned step 2 is regained to be repeated. Otherwise, a succeeding step 6 is executed where the beam index of the probe 14 (i.e. the point of incidence of the beam emitted by the probe 14) is aligned with the reference point A and the rotational angle of the probe about the $\theta$-axis is set to a scale reference value of zero degree.

Next, the reference point data of the scanning unit 10 are loaded in the data collecting/recording unit 30 at a step 7 (denoted by ST 7 in FIG. 4), which is followed by a step 8 where the beam index of the probe 14 is aligned with the reference point B, whereupon the coordinates of the reference point B are inputted to the data collecting/recording unit 30 at a step 9. Thereafter, the mnual flaw detection process is carried out by moving the probe 14 in a zig-zag fashion (step 10). In the course of this manual scanning operation, an ultrasonic pulse signal is emitted toward the interior of the material 40 under test through the probe 14 by the ultrasonic flaw detector 20 (step 11). The ultrasonic echo signal produced by reflection of the emitted ultrasonic pulse signal at a flaw or defect within the weld 41 of the material 40 under test is received by the probe 14 to be converted into an electric signal which is then fed to the ultrasonic flaw detector 20 (step 12). The latter then performs analysis of the flaw on the basis of the so-called reflection echo signal, the results of which are displayed on the CRT 21, while the flaw detection data (beam path distance or length and echo height) is outputted to the data collecting/recording unit 30 (step 13). The CPU 32 incorporated in the unit 30 makes decision as to whether the flaw detection data is valid or not (step 14). If the result of the decision step 14 is negative (N), the step 10 is regained and the processing following the step 10, inclusive, is repeated in the same manner as described above. If otherwise (Y), the probe position data (displacements of the probe along the X- and Y-axes, rotational angle of the $\theta$-axis) at that time point are fetched from the scanning unit 10 (step 15). Subsequently, the CPU 32 makes a decision as to whether the probe position data are the same as those obtained through execution of the preceeding scanning operation at step 16. If so (Y), the step 10 is regained. Otherwise (N), the probe position data and the relevant flaw detection data are stored im the memory 33 of the data collecting/recording unit 30. Next, at a step 18, it is decided whether the processing and operation described above have been performed over the whole region 41 of the material 40 under test (step 18). If so, the flaw detection data and the probe position data stored in the memory 33 of the data collecting/recording unit 30 are transferred to the external recording or storing medium 34 such as cassette tape, floppy disc or the like at a step 19.

Through the processing and operation described above, the raw data of the probe position (data concerning displacements of the probe along the X- and Y-axes and rotational angle about the $\theta$-axis) as well as the flaw detection data (data of beam path length and echo height) can be easily collected and recorded in situ (i.e. in the field) with a high reliability.

In this manner, the raw data, i.e. the flaw detection data and the probe position data are collected and recorded on the external recording medium 34 in situ. The external recording medium 34 is then transported to the central station where it is loaded in the data processing apparatus 60 to perform classification or graduation of flaws in accordance with, for example, the JIS standards as well as plotting of the cross-sectional profiles or patterns (longitudinal and transversal sections) and the plan profiles of flaw and preparation of other data.

The invention also provides a method of determining the flaw position in the course of the ultrasonic flaw detecting operation carried out according to an embodiment of the invention, which method will be described by referring to FIGS. 5 to 8.

More specifically, in the ultrasonic flaw detecting system which comprises the scanning unit 10 composed of the X-axis member 11 mounted on a material 40 under test in parallel with the weld line 42, the Y-axis arm member 12 mounted on the X-axis base member 11 movably along the longitudinal axis thereof and the probe 14 supported by the Y-axis arm member 12 longitudinally movably and universally rotatably, and the data collecting/recording unit 30 for recording on the recording medium 34 the flaw detection data as well as the position data of the probe 14 of the scanning unit, wherein the data stored in the recording medium 34 is inputted to the data processing apparatus 60 for performing data analysis, as described above, it is proposed according to an embodiment of the invention a flaw position determining method which comprises a step of aligning the beam index of the probe 14 with the first reference point A on the weld line 42 of the material under test to establish the coordinates of the reference point A in the X- and Y-coordinate system defined by the X- and Y-axes members as well as the reference point of scale which corresponds to the probe rotational angle $\theta$ of zero, a step of moving the probe 14 from the first reference point A to the second reference point B marked on the weld line 42 to establish the positional coordinates of the second reference point B in the X- and Y-coordinate system, a step of determining the beam index, i.e. the point of incidence of the beam emitted by the probe 14 with reference to the weld line 42 on the basis of the coordinates of the first and second reference points A and B, a step of determining a linear distance on a plane between the probe 14 and a flaw as detected on the basis of the angle of inclination (also referred to as tilt angle) of the probe 14 and the beam path distance to the flaw, and a step of determining the position of the flaw on the basis of the coordinates of the beam index of the probe 14 with reference to the weld line 42, the rotation angle of the probe and the linear distance on a plane to the position of the flaw.

Figure 5:
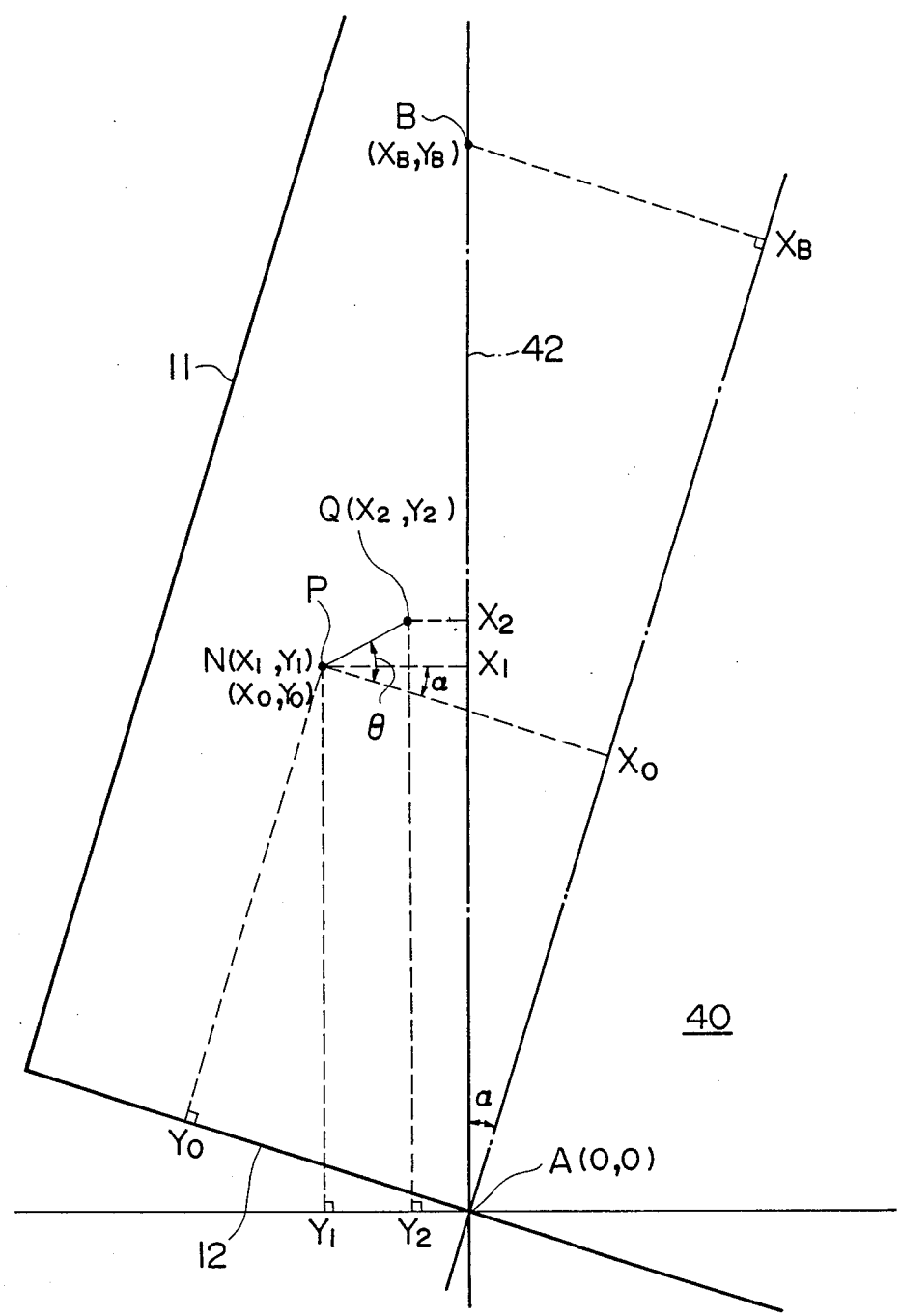
FIG. 5 is a view for illustrating a first example of the state in which the scanning unit employed in the ultrasonic flaw detecting system according to the invention is positioned on a material to be examined and a flaw detection coordinate system for the probe.

For carrying out the method of determining or locating the flaw position, the scanning unit 10 is placed on the material 40 under test with the beam index P of the probe 14 being aligned with the rotational axis of the manipulating rod 19 of the probe holder 13, as is shown in FIG. 5. In this state, the X-axis base member 11 is positioned at a random angle relative to the weld line 42 of the material 40 under test. Next, as will be seen in the flow chart of FIG. 6, the beam index P of the probe 14 is aligned with the first reference point A on the weld line 42 and the rotation angle $\theta$ of the probe in this aligned state is set to the scale value of zero degree (step 21), being followed by the setting of the coordinates of the point A in the X-Y coordinate system (i.e. coordinate system defined by the X-axis base member 11 and the Y-axis arm member 12) to a value A(O,O) which is employed as the reference point of scale (step 22). Subsequently, the beam index P of the probe 14 is aligned with the second reference point B on the weld line 42 which point B may be located at an arbitrarily selected position within the length of the X-axis base member 11 (step 23) to obtain the data of coordinates $(X_B, Y_B)$ of the point B in the X-Y coordinate system (step 24). Subsequently, flaw searching is started through manual scanning with the probe 14 in a zig-zag fashion (step 25). At that time, an ultrasonic pulse signal is injected into the material 40 from the ultrasonic flaw detector 20 through the probe 14 at a predetermined angle (angle of refraction) $\phi$ (step 26). Upon reflection of the ultrasonic wave at a flaw present in the weld 41 of the material 40 under test, an ultrasonic echo signal is produced and caught by the probe 14 to be converted into an electrical signal. The latter is transmitted to the ultrasonic flaw detector 20 (step 27), which then analyzes the flaw on the basis of the echo data, the result of analysis being displayed on the CRT, while the flaw detection data such as beam path length W and magnitude or height of echo or ultrasonic reflection H (also referred to as echo height) at that time are supplied to the data collecting-/recording unit 30 (step 28) for making decision as to whether the flaw detection data is of a valid flaw or not (step 29). If the flaw data is proven invalid, the processing at the step 25 is regained to perform again the seried of operations mentioned above. On the other hand, when the data is of a valid flaw, the flaw detection data W and E as well as position data including the coordinate data $N(X_O, Y_O)$ of the probe along the X- and Y-axes members 11 and 12 (which corresponds to the position data $X_1$ and $Y_1$, respectively, on the scanning unit) and the rotation angle $\theta$ are fetched by the data collecting/recording unit 30 (step 30). Subsequently, it is determined whether the flaw searching operation has been performed for the whole range of the weld 41 of the material 40 under test (step 31). If so, the flaw detection data and the position data stored in the data collecting/recording unit 30 are transferred to the external recording medium 34 such cassette tape, floppy disc or the like (step 32).

The flaw detection data of the material 40 tested and the position data collected and recorded in situ in this manner are thereafter inputted to the data processing unit 60 for the analysis. In this connection a process of determining the position of the flaw will be described by referring to the flow chart shown in FIG. 7. In the first place, at a step 33, the linear distance L on a plane from the beam index or point of incidence P of the ultrasonic beam to the flaw Q is determined on the basis of the beam path length or distance W and the preset beam angle $\phi$ (angle of inclination of the probe 14) in accordance with $$L = W_O \sin \phi (mm)$$

and $$W_o = W \times V/2$$

where
W: beam path length ($\mu S$) inputted at the step 30, and
V: sound velocity (m/S)

Next, at a step 34, the angle $\alpha$ of the scanning unit 10 on the material 40 under test relative to the weld line 42 is determined on the basis of the position data of the points A and B by solving the following equations:

$$K = \sqrt{X_B^2 + Y_B^2}$$

$$\tan \alpha = Y_B/X_B$$

$$\cos \alpha = X_B/K$$

$$\sin \alpha = Y_B/K$$

where K represents the distance between the points A and B.

Further, at a step 35, the position coordinates $N(X_1, Y_1)$ of the beam index P of the probe 14 with reference to the weld line 42 is determined on the basis of the angle $\alpha$ at which the scanning unit 10 is disposed relative to the weld line 42 and the position data $N(X_o, Y_o)$ in accordance with $$X_1 = (Y_o - X_o \cdot \tan \alpha) \sin \alpha + X/\cos \alpha$$

$$Y_1 = (Y_o - X_o \cdot \tan \alpha) \cos \alpha$$

Finally, at a step 36, the flaw position Q(K, Y) is determined on the basis of the rotational angle $\theta$ of the probe 14, the positional coordinates $N(X_1, Y_1)$ relative to the weld line and the linear distance L in accordance with $$X_2 = L \sin(\theta - \alpha) + (Y_o - X_o \tan \alpha) \sin \alpha + X_o/\cos \alpha$$

$$Y_2 = (Y_o - X_o \tan \alpha) \cdot \cos \alpha - L \cos(\theta - \alpha)$$

The flaw position Q thus determined is printed out.

For determination of the depth d of a flaw, the linear distance L on a plane from the beam index P of the probe 14 to the flaw position Q is determined as mentioned above (step 33) and additionally a distance $L_1$ to a skip point is determined in accordance with $$L_1 = t_1 \times \tan \phi$$

where
$t_1$: thickness of the sheet material under test, and
$\phi$: beam angle (angle of refraction)

Further, a multipule S of a skips to the flaw position is determined as follow:

$$S = INT(L/L_1)$$

When the skip multiple S is of an odd number, the flaw depth d is given by $$d = t_1(S+1) - W_o \cos \phi$$

In case the skip multiple S is of an even number, the depth d is given by $$d = W_o \cos \phi - t_1 \cdot S$$

As will be understood from the above elucidation, by virtue of such arrangement that the angle $\alpha$ at which the scanning unit 10 is disposed is arithmetically determined on the basis of a pair of reference points A and B on the weld line 42, wherein the positional coordinates of the scanning unit 10 with reference to the weld line 42 can be determined on the basis of the angle $\alpha$, it is possible to place the scanning unit 10 at random on the material to be inspected, simplifying thus the procedure for positioning the scanning unit 10. Further, since the movable componrents are moved linearly, the trigonometric expressions involved in the calculations can be simplified, which means that the arithmetic processing can be performed at an increased rate, to another advantage.

Figure 9:
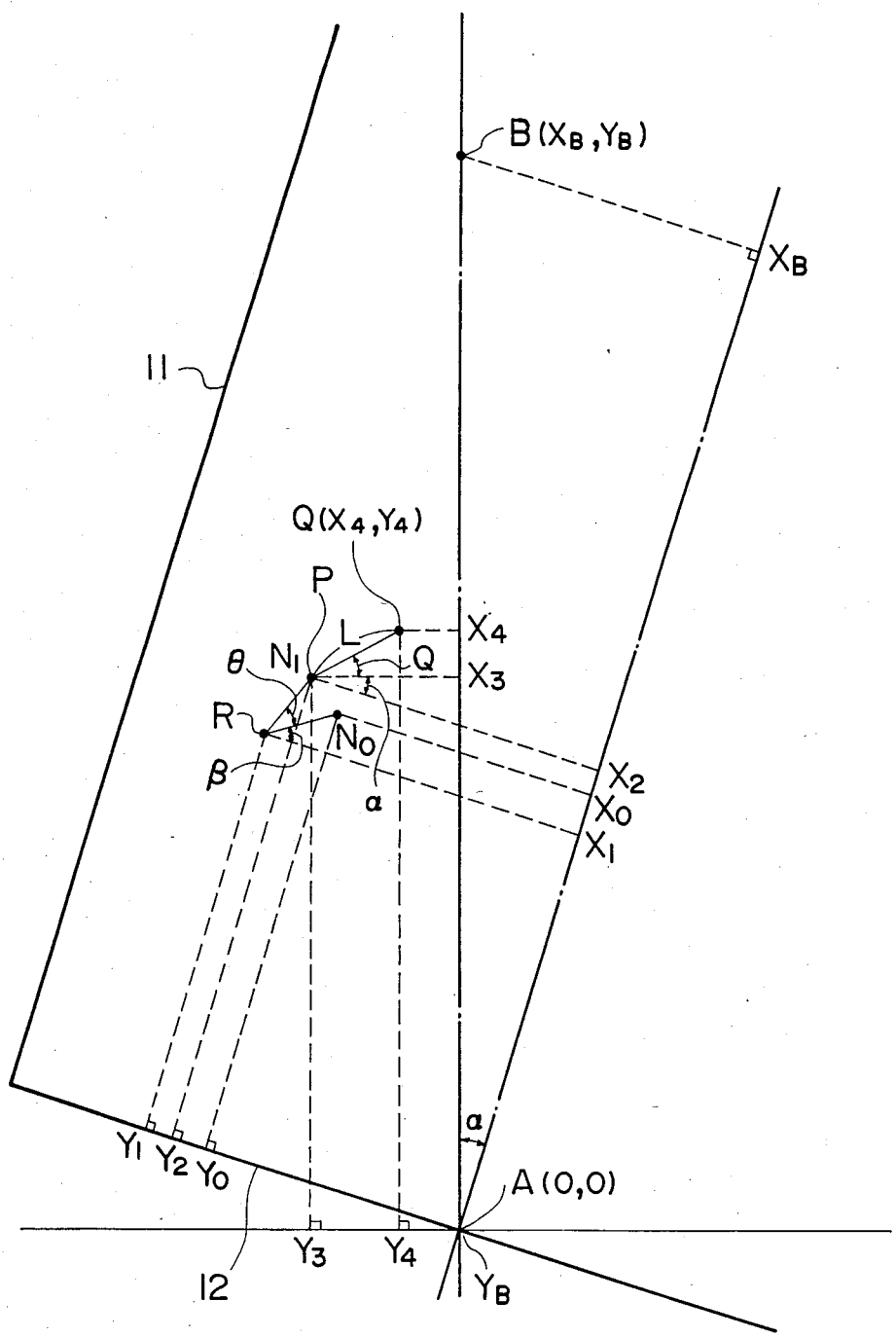
FIG. 9 is a view for illustrating a second example of the state in which the scanning unit employed in the ultrasonic flaw detecting system according to the invention is positioned on a material to be examined and a flaw detection coordinate system for the probe.
Figure 10:
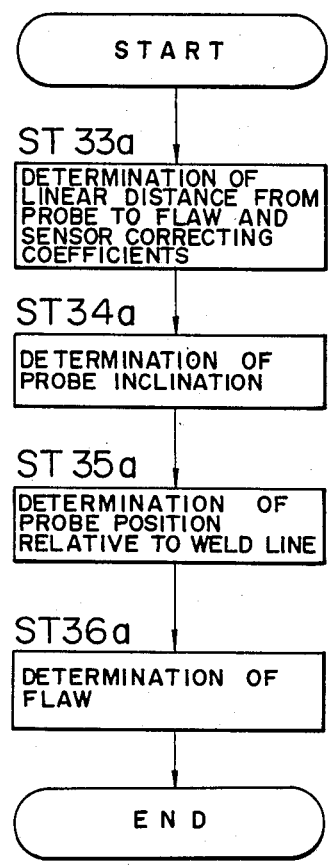
FIG. 10 is a view similar to FIG. 7 for illustrating in a flaw chart a process of locating a flow based on the flaw detecting operation of the scanning unit in the flaw detection coordinate system according to the second example.

FIGS. 9 and 10 illustrate the flaw locating method according to another embodiment of the invention for determining the position of a flaw detected in the course of the ultrasonic flaw detecting operation. The method illustrated in FIGS. 9 and 10 is based on the substantially same concept as the method described above but improved over the latter in respect that the determination of flaw position can be accomplished with high accuracy even when there is produced deviation between the beam index P and the center of rotation of the probe 14 due to abrasion of the flaw searching surface thereof.

Figure 6:
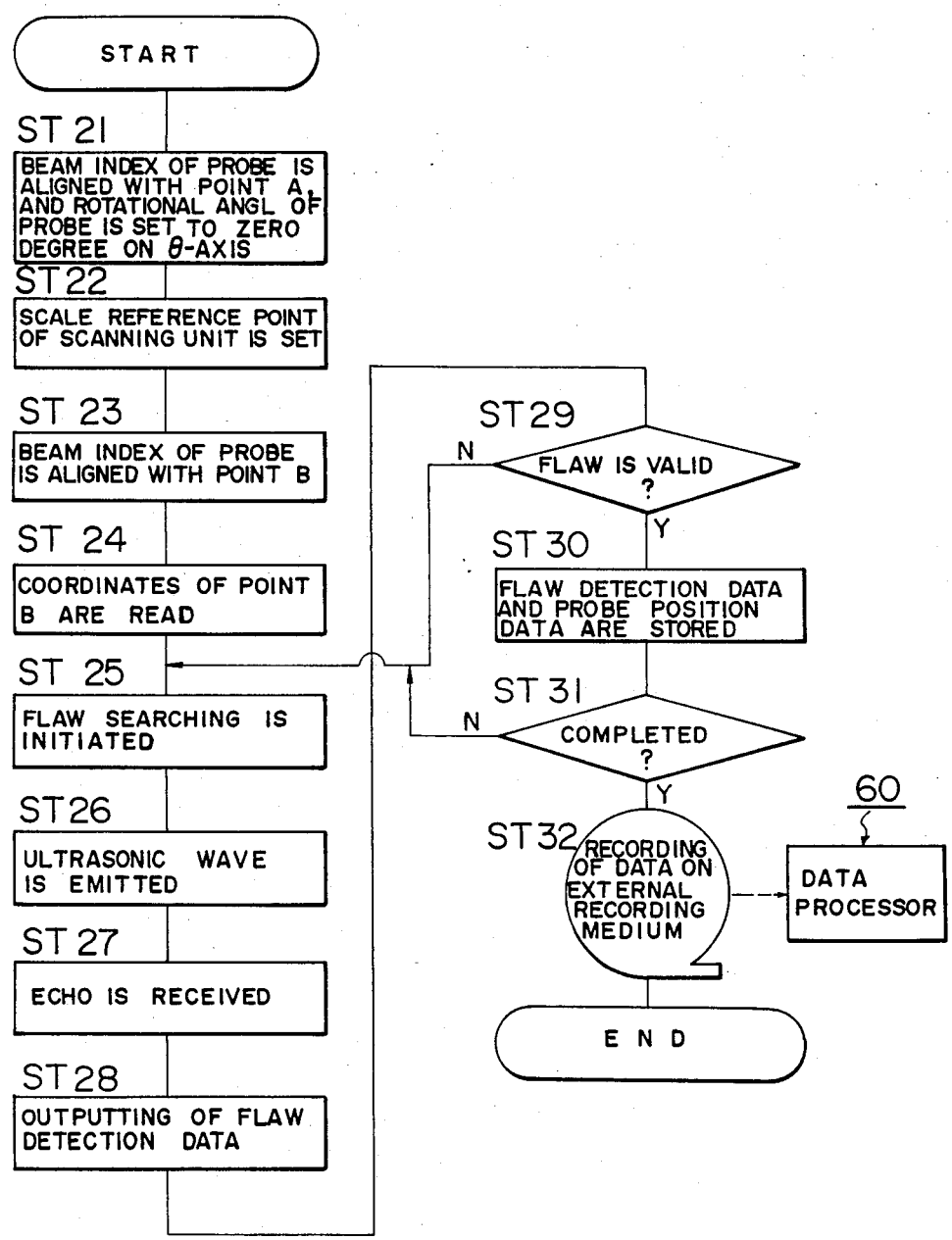
FIG. 6 is a flow chart for illustrating the flaw detecting operation performed by the scanning unit on the flaw detection coordinate system according to the first example.
Figure 7:
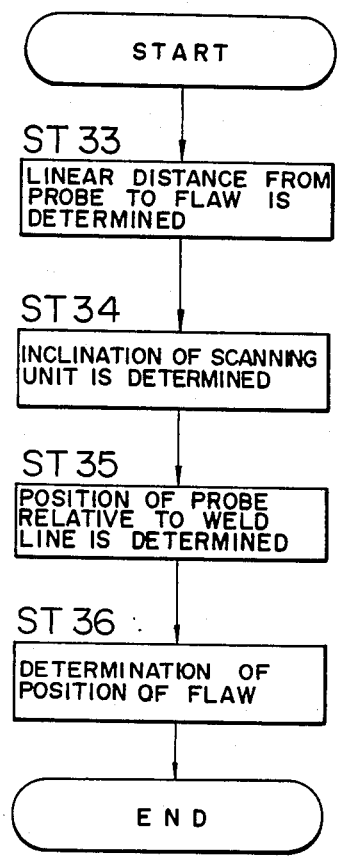
FIG. 7 is a flow chart for illustrating a process of locating the position of a flaw based on the flaw detecting operation of the scanning unit in the flaw detection coordinate system according to the first example.

In carrying out the method according to the instant embodiment, the scanning operation as well as the flaw detection data collecting recording is implemented in the utterly same manner as described hereinbefore by referring to FIG. 6.

The flaw detection data and the position data of a test material 40 collected and recorded in situ are loaded in the data processing apparatus 60 installed at a remote location such as a central control room. Referring to the flow chart shown in FIG. 10 in combination with FIG. 9, a linear distance on a plane between the beam index P and the flaw position Q is determined on the basis of the beam path length $W_O$ contained in the flaw detection data and the preset beam angle $\phi$ of the probe 14 in accordance with $$L = W_O \sin \phi (mm)$$

where
$W_O = W \times V/2$,

W: beam path length ($\mu S$) read in at the step 30, and
V: sound velocity (m/s)

Further, distance Z between the beam index P and the center R of rotation of the probe 14 as well as a sensor correction coefficient of inclination $\beta$ is determined from the positional coordinates $N_O(X_O, Y_O)$ of the probe 14 whose rotational angle $\theta$ is zero at a step 33a. When the positional coordinates of the center of rotation of the probe 14 is represented by $R(X_1, Y_1)$, the positional coordinates $N_1(X_2, Y_2)$ of the beam index P with reference to the scanning unit 10 are given by $$X_2 = X_1 + Z \sin(\beta + \theta)$$

$$Y_2 = Y_1 + Z \cos(\beta + \theta)$$

Subsequently, at a step 34a, the angle $\alpha$ at which the scanning unit 10 is disposed or orientated on the material 40 with reference to the weld line 42 is determined from the position data of the points A and B in accordance with $$K = \sqrt{X_B^2 + Y_B^2}$$

$$\tan \alpha = Y_B/X_B$$

$$\cos \alpha = X_B/K$$

$$\sin \alpha = X_B/K$$

where K represents the distance between the reference points A and B.

Next, at a step 35a, the positional coordinates $N_1(X_3, Y_3)$ of the beam index P with reference to the weld line 42 are determined from the orientation angle $\alpha$ and the position data $N_1(X_2, Y_2)$ in accordance with $$X_3 = (Y_2 - X_2 \cdot \tan \alpha) \sin \alpha + X_2/\cos \alpha$$

$$Y_3 = (Y_2 - X_2 \cdot \tan \alpha) \cos \alpha$$

Finally, at a step 16, the position $Q(X_4, Y_4)$ of a flaw is determined on the basis of the rotational angle $\theta$ of the probe 14, the positional coordinates $N_1(X_3, Y_3)$ thereof with reference to the weld line, the linear distance L and the sensor correction coefficients Z and $\beta$ in accordance with $$\begin{aligned} X_4 &= L \sin(\theta - \alpha) + (Y_2 - X_2 \tan \alpha)\sin \alpha + \frac{X_2}{\cos \alpha} \\ &= L \sin(\theta - \alpha) + \{[Y_1 + Z \cos(\beta + \theta)] - \\ &\quad [X_1 + Z \sin(\beta + \theta)]\tan \alpha\} \times \sin \alpha + \frac{X_1 + Z \sin(\beta + \theta)}{\cos \alpha} \end{aligned}$$

$$\begin{aligned} Y_4 &= (Y_2 - X_2 \cdot \tan \alpha) \cdot \cos \alpha - L \cos(\theta - \alpha) \\ &= \{[Y_1 + Z \cos(\beta + \theta)] - \\ &\quad [X_1 + Z \sin(\beta + \theta)]\tan \alpha\}\cos \alpha - L \cos(\theta - \alpha) \end{aligned}$$

The obtained position data Q is printed out.

Figure 8:
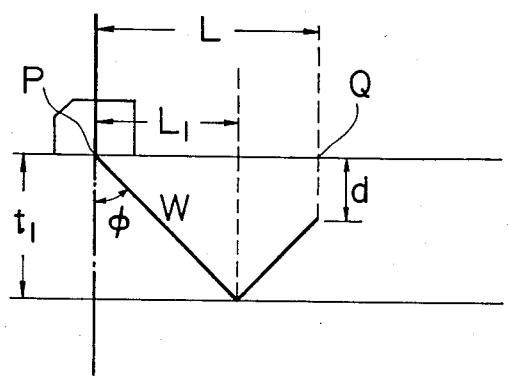
FIG. 8 is a view for illustrating positional relationship between a point of incidence of an ultrasonic beam emitted by the probe (also referred to as the beam index) and a flaw.

The depth d of the flaw can be determined in the substantially same manner as described hereinbefore in conjunction with FIG. 8.

FIGS. 11 and 12 are views showing an exemplary embodiment of the flaw detection data collecting/recording unit which can be employed in the ultrasonic flaw detecting system according to the present invention. This flaw detection data collecting/recording unit is provided with a digital display for displaying at least the position data of the probe constituting a member of the flaw detection data set.

With the arrangement of the flaw detection data collecting/recording unit according to the instant embodiment, it is possible to display digitally the probe position data (i.e. displacements along the X- and Y-axis members and rotational angle $\theta$ of the probe). By virtue of this feature, the position of the manual scanning unit including the probe along the X- and Y-axes can be determined with a high accuracy and reliability by observing the digital display instead of simply relying on the eye-measurment as in the case of the hitherto known apparatus. More specifically, the position of the probe at which a flaw is actually detected can be confirmed through comparison of the result of eye-measurement with the digital display. It is self-explanatory that coincidence between the eye-measurement and the content of the digital display means that the flaw detection data (i.e. the probe position data and the flaw data) have been collected and recorded with high reliability. Further, simplicity of the confirmation by the digital display relieves operator from mental strain which would otherwise accompany the flaw detecting operation. Besides, failure or malfunction of the apparatus can be easily detected, to another advantage.

The flaw detection data collecting/recording unit can be so implemented as to display digitally the flaw data (i.e. beam path length and echo height) in addition to the probe position data. In that case, abnormality in operation or malfunction of the manual scanning unit and the ultrasonic flaw detector can be easily discovered.

More specifically, FIG. 11 is a front view of the flaw detection data collecting/recording unit 30, and FIG. 12 is a block diagram showing a general arrangement of the same. In this exemplary embodiment of the invention, the unit is so implemented that the flaw data and the probe position data can be digitally displayed. Referring to FIGS. 11 and 12, a reference numeral 36 denotes a display field for displaying digitally both the flaw data and the probe position data. The display field 36 includes an X-axis display 361 for displaying digitally the displacement of the probe along the X-axis member, a Y-axis display 362 for displaying digitally the displacement along the Y-axis member, and a $\theta$-axis display 363 for displaying digitally the rotational angle of the $\theta$-axis or holder 13, all of the aforementioned data being supplied from the scanning unit as the probe position data. The display field 36 further includes an E-display 364 for displaying digitally the data of echo height E and a W-display 365 for displaying digitally the data of the beam path length or distance W, both data E and W being transmitted from the ultrasonic flaw detector 20 as the flaw data. A reference numeral 37 denotes a manipulating field which includes a main switch 371 for electrically connecting the apparatus to an AC or DC power supply source such as battery, a lamp 372 for displaying ON/OFF state of the switch 374, and a ready lamp 373 for informing by flickering that the apparatus is in the state ready for performing the flaw detecting operation, a display mode change-over pushbutton switch (hereinafter referred to also as PB switch) 374 for changing over the display mode of the display field 36 as described hereinafter, a position lamp (hereinafter referred to also as POSI lamp) 375 which is lit, extincted and flickered in response to the turn-on of the PB display switch 374, and other plural switches and lamps. A reference numeral 38 denotes a recorder for recording on a recording medium 34 the flaw detection data, i.e. the flaw data and the probe position data which are digitally displayed.

The flaw data collecting/recording unit 30 includes a CPU 32 performing processings for fetching and displaying digitally the flaw detection data and the data recording, a memory 33 for storing temporarily the flaw detection data fetched by the CPU 32, an X-, Y- and $\theta$-axes interface 31a for allowing the probe position data to be loaded in the CPU 32 from the scanning unit 10 through the transmission line 51, an E/W interface 31b for allowing the flaw data to be loaded in the CPU 32 from the ultrasonic flaw detector 20 through the transmission line 51, an input interface 39 for allowing the display change-over signal of the PB display switch 374 to be loaded in the CPU 32, an output interface 45 for energizing the ready lamp 373 and the POSI lamp 375 in dependence on the command issued by the CPU 32, a digital display interface 46 for energizing the displays 361 to 365 of the display field 36, and a data collecting/recording interface 47 for allowing the flaw detection data to be transferred from the CPU 32 to the recorder 38.

Only when it is decided by the CPU 32 that the flaw detection data signal inputted to the flaw data collecting/recording unit exceeds a predetermined level, indicating detection of a flaw by the probe 14, the displays 361 to 365 of the display field 36 display the data of the detected flaw and the associated probe position data until a flaw is next detected (this mode is referred to as the flaw detection data display mode). On the other hand, so long as no flaw is detected, the probe position data, i.e. the data of position of the probe along the X-, Y- and θ-axes with reference to point A are digitally displayed by the displays 361 to 363 on the real-time basis (this mode will be referred to as the continuous position display mode). Accordingly, in the flaw detection data display mode, the flaw detection data including the flaw data and the associated probe position data which have been recorded latest are displayed digitally. On the other hand, in the continuous position display mode, the current position data of the scanning unit 10 along the X-, Y- and θ-axes are digitally displayed on the displays 361 to 363 on the real time basis. In this case, the E-display 364 and the W-display 365 may display "Os", respectively.

In the case of the illustrated embodiment, it has been described that the display field 36 includes a number of independent displays 361 to 365. However, it is also possible to provide only one display for displaying digitally the probe position data or the flaw data.

With the flaw detection collecting and recording unit of the structure described above, a method of fetching the flaw detection data may be carried out in a manner illustrated in FIGS. 13 to 16. According to this method, the flaw data which are produced by the ultrasonic flaw detector 20 connected to the scanning unit 10 which scans the test surface of the material 40 are sampled when the flaw data meet predetermined conditions, and at the same time the probe position data supplied from the scanning unit 10 are sampled, wherein both sampled data are temporarily stored. The data thus sampled currently are compared with the corresponding preceding data, respectively. When the difference between any data exceeds a predetermined value, the data sampled currently are stored in the memory 33 of the flaw detection data collecting/recording unit 30 to be subsequently transferred to the external recording medium 34 as the raw flaw detection data.

Since any flaw detection data as fetched is necessarily compared with those fetched precedingly, the possibility of the flaw detection data being sampled repeatedly at a same position on the test surface or the possibility of the same flaw detection data being fetched at other location can be positively excluded, whereby only the valid data appropriate to the flaw detection can be fetched without duplicate, which in turn means that the amount of data to be stored in the memory of a given capacity can be increased when compared with the method in which the data are loaded at random. In other words, the memory can be utilized more efficiently.

Figure 13A:
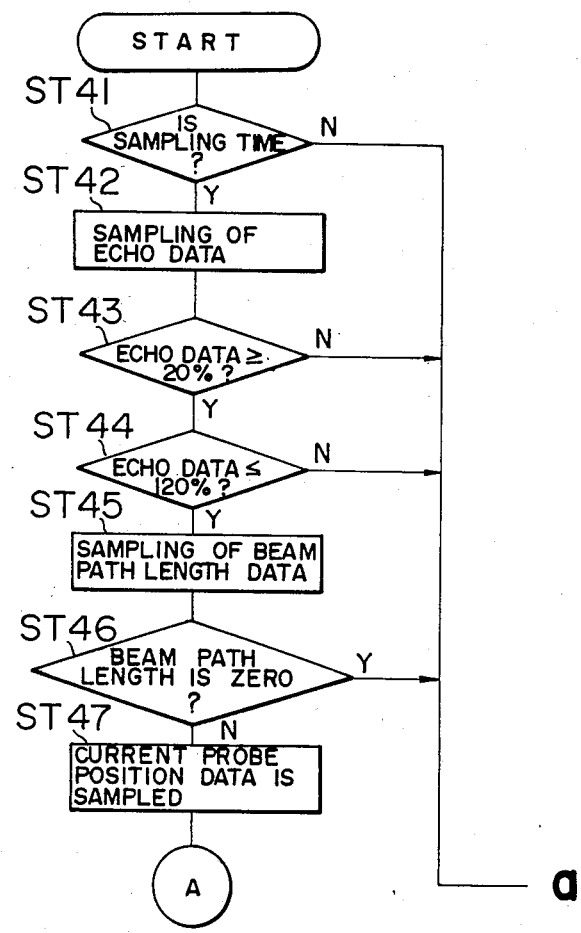

Now, the flaw detection data fetching method outlined above will be described in detail by referring to the flow chart shown in FIG. 13.

At first, initialization processing including the turning-on of the power supply, alignment of the probe 14 of the manual scanning unit 50 with the points A and B are effected. Upon initiation of flaw searching operation through manual scanning, a counter incorporated in the CPU 32 produces a timing signal (step 41) at which the echo data from the ultrasonic flaw detector 20 is sampled (step 42). It is assumed that the echo data sampled at this time is represented by E2. Further, the sampling period t (FIG. 14) is set at 20 ms which can be altered by changing or rewriting a relevant memory constant. Subsequently, at steps 43 and 44, decision is made as to whether or not the echo data E2 origins in a true flaw, i.e. whether the echo data is valid or not.

In that case, a reference range C is established which is defined by an upper limit H corresponding to 120% of a valid echo height E previously determined from experimental measurements and given in terms of a voltage level and a lower limit L corresponding to 20% of that voltage level. When the echo E falls within the range C, it is decided that the echo E2 origins in a valid flaw. In FIG. 15, a symbol S denotes magnitude of beam energy emitted by the probe 14, and W denotes the beam path length. So far as the beam path length is zero, it is decided that the echo signal is not valid, even if the echo height lies in the range C. The decision as to whether the flaw data (i.e. echo data and the beam length data) lie within the predetermined reference range is performed by the CPU 32.

More specifically, at a step 43, decision is made as to whether the aforementioned echo data E2 is higher than the lower limit of 20%. When the echo data E2 subsequently determined lower than the upper limit of 125% at a step 44, the echo data is temporarily stored in the memory 33. At that time, the beam path length data W supplied from the ultrasonic flaw detector 20 and corresponding to the echo data E2 is sampled at a step 45. It is assumed that the beam path length data sampled currently is represented by W2. Next, the beam path length data W2 is checked as to whether it is zero or not at a step 46. Unless it is zero, the data W2 is temporarily stored in the memory 33. At the same time, the probe position data X, Y and O, i.e. the position data of the probe along the X-, Y- and θ-axes supplied from the manual scanning unit 10, are sampled to be stored temporarily at a step 47. Again, it is assumed that the X-axis position data, Y-axis position data and the θ-axis position data thus sampled are represented by X2, Y2 and θ2, respectively.

The flaw detection data (X2, Y2, θ2, W2, E2) sampled at this time are compared with the preceding flaw detection data D1 stored in the memory 33, which data (D1) includes the X-axis position data X1, Y-axis position data Y1, θ-axis position data θ1, beam ptah length data W1 and the echo data E1.

More specifically, at a step 48, difference between the X-axis position data X2 and X1 is arithmetically determined, wherein decision is made as to whether the difference exceeds a predetermined value (e.g. +1 mm). At a step 49, difference between the Y-axis position data Y2 and Y1 is arithmetically determined and checked as to whether the difference exceeds a predetermined value (e.g. +1 mm). Similarly, at a step 50, the θ-axis position data θ2 and θ1 are compared with each other and it is determined whether the difference exceeds a predetermined value (e.g. +0.5 degree). At a step 51, difference between the beam path length data W2 and W1 is arithmetically determined and checked as to whether the difference exceeds a predetermined value (e.g. +1 mm). At a step 52, information indicative of the presence of a flaw is issued when any one of the aforementioned differences exceeds the associated reference value. At the same time, the sampled flaw detection data (X2, Y2, θ2, W2 and E2) are stored in the memory 33 at a step 53. In that case, the currently sampled flaw detection data (X2, Y2, θ2, W2, E2) are stored independent of the precedingly sampled flaw detection data (X1, Y1, θ1, W1, E1).

On the other hand, when there are no differences which exceed respective predetermined reference values at the aforementioned steps 48 to 51, the currently sampled echo data E2 is compared with the preceding echo data E1 to decide whether the difference therebetween exceeds a predetermined value. In the case of the illustrated example, it is decided whether the current echo data E2 is of more significance than the preceding echo data. If so, it is determined that the predetermined value is exceeded, as a result of which information indicative of the presence of a flaw is produced (step 55). At that time, all of the currently sampled flaw detection data (X2, Y2, θ2, W2, E2) may be stored in the memory 33. However, in the illustrated case, only one member of the data, i.e. the echo data E2, is stored in the memory 33. In that case, the echo data E1 of the preceding flaw detection data (X1, Y1, θ1, W1, E1) is replaced by the current echo data E2 at a step 56. Thus, the memory 33 stores therein the flaw detection data consisting of the preceding data X1, Y1, θ1 and W1 and the current echo data E2, as is shown in FIG. 16(a).

The flaw detection data stored in the memory 33 through the procedure described above (refer to FIG. 16) can now be transferred to the external recording medium 34 through the data recording interface 47.

It should be mentioned that the reference range as well as reference values mentioned above can be set and altered in a rather arbitrary manner. Accordingly, by selecting the reference range and the reference values in dependence on the intended applications, the flaw detection data can be obtained with high reliability.

The method of classifying or graduating the flaws detected through the data processing apparatus used in the ultrasonic flaw detection system according to the invention resides in that reference data is obtained by testing a calibration block for test while the flaw detection data are obtained from a material under test, by means of the probe and the ultrasonic flaw detector or through the manual scanning unit equipped with the probe and the ultrasonic flaw detector. The flaw detection data obtained are once recorded on a recording medium and subsequently loaded into the separate data processing apparatus which is additionally loaded with the thickness data of the material under test and other data required for the flaw classification. The data processing apparatus creates a distance-vis-amplitude characteristic curve by arithmetically processing the aforementioned reference data and determines the range of the echo height on the basis of the characteristic curve and the flaw detection data. On the other hand, the flaw detection data are subjected to a coordinate transformation to be converted to point data with reference to the weld line. When the distance between the adjacent point data is within a predetermined range, the point data are synthesized into line data. Further, when distance between the adjacent line data satisfy predetermined conditions, the line data are regarded as belonging to a same flaw and synthesized. Otherwise, the line data are regarded as belonging to different independent flaws, respectively, and processed to arithmetically determine the indicated flaw or defect length. The flaw classification is then effected in accordance with the JIS standards on the basis of the data of indicated defect length, the range of echo height and the thickness.

The above mentioned flaw classification method according to the invention allows the classification of the detected flaw with higher reliability and accuracy when compared with the automatic flaw detecting procedure, because the flaw detection data which provide base data for the classification can be carefully collected and recorded. Further, since the classification processing can be executed completely automatically, the result as obtained will never be influenced by the skill of operator, whereby errors usually involved in calculation, reading, recording and others can be evaded, while assuring rapid and accurate processing and hence the classification of high reliability and accuracy.

In the foregoing, the invention has been described in detail in conjunction with preferred embodiments. It should however be appreciated that the invention is never restricted to these illustrated embodiment. Numerous modifications and variations will readily occur to those skilled in the art without departing from the spirit and scope of the present invention.

What is claimed is:

1. A method of locating a flaw position in a weld line of a material to be tested with an ultrasonic scanning unit comprising the steps of:

placing said scanning unit having a probe over said material to be tested at a random angle relative to said weld line, said probe producing probe position data including data of displacements of said probe along an X-axis and a Y-axis and a rotational angle of Θ axis;

aligning a beam index P of said probe with a first reference point A on said weld line of said material to be tested, and reading positional coordinates of said first reference point A in an X and Y coordinate system;

aligning said beam index P of said probe with a second reference point B lying on said weld line a given distance from said first reference point A, and reading the positional coordinates of said second reference point B in said X and Y coordinate system;

transmitting an ultrasonic signal from an ultrasonic flaw detector to said probe and producing flaw detection data on the basis of a reflection echo signal fed back from said probe;

receiving said flaw detection data from said ultrasonic flaw detector and said probe position data from said scanning unit and recording both of said data on an external recording medium; and processing said data recorded on said external recording medium to locate the flaw position in said weld line of said material to be tested.

2. A method of locating a flaw position in a weld line of a material to be tested according to claim 1 wherein an angle α at which said scanning unit is disposed relative to said weld line is determined on the basis of the positional coordinates of said first and second reference points A and B, positional coordinates $N(X_1, Y_1)$ of the beam index of said probe relative to said weld line at a position where a flaw is detected are determined on the basis of said angle $\alpha$, a linear distance L on a plane between the beam index of said probe and the position Q of the detected flaw is determined on the basis of a preset beam angle $\phi$ of said probe and a beam path length to said flaw, and positional coordinates $(X_2, Y_2)$ of said flaw relative to said weld line is determined in accordance with $$X_2 = L \sin(\Theta - \alpha) + (Y_O - X_O \tan \alpha) \cdot \sin \alpha + X_O / \cos \alpha$$

$$Y_2 = (Y_O - X_O \tan \alpha) \cdot \cos \alpha - L \cos(\Theta - \alpha)$$

wherein $(X_O, Y_O)$ represent coordinates of the probe of said scanning unit at the position of said flaw in said X and Y-coordinate system.

3. A method of locating a flaw position in a weld line of a material to be tested according to claim 1 wherein an angle $\alpha$ at which said scanning unit is disposed relative to said weld line is determined on the basis of the positional coordinates of said first and second reference points A and B, positional coordinates $N_1(X_3, Y_3)$ of the beam index of said probe relative to said weld line at a position where a flaw is detected are determined on the basis of said angle $\alpha$, a linear distance L on a plane between the beam index of said probe and the position Q of the detected flaw is determined on the basis of a preset beam angle $\phi$ of said probe and a beam path length to said flaw, and positional coordinates $(X_4, Y_4)$ of said flaw relative to said weld line are determined in accordance with $$X_4 = L \sin(\theta - \alpha) + \{[Y_1 + Z \cos(\beta + \theta)] - [X_1 + Z \sin(\beta + \theta)] \tan \alpha\} \sin \alpha + \frac{X_1 + Z \sin(\beta + \theta)}{\cos \alpha}$$

$$Y_4 = \{[Y_1 + Z \cos(\beta + \theta)] - [X_1 + Z \sin(\beta + \theta)] \tan \alpha\} \cos \alpha - L \cos(\theta - \alpha)$$

where Z represents a distance between the beam index of said probe and a center of rotation of said probe, and $\beta$ represents inclination of a line interconnecting the beam index of said probe and said center of rotation relative to said scanning unit, and $(X_1, Y_1)$ represent positional coordinates of said center of rotation of said probe relative to sid scanning unit.

4. A method of locating a flaw position in a weld line of a material to be tested according to claim 1 further comprising the step of displaying digitally said probe position data and the flaw data only in a flaw detection operating mode and otherwise displaying digitally the probe position data.

5. A method of locating a flaw position in a weld line of a material to be tested according to claim 1 wherein the flaw data falling within a predetermined reference range is sampled, which data is supplied from the ultrasonic flaw detector connected to the scanning unit for scanning a test surface of the material under test and at the same time the probe position data supplied from said scanning unit is sampled, both data being stored temporarily and compared, respectively, with the corresponding data sampled precedingly, and wherein in case any one of differences resulting from said comparisons exceeds a predetermined value, the data sampled currently are stored in a memory incorporated in said flaw detection data collecting/recording unit and subsequently transferred to an external storage medium as the raw flaw detection data.

6. A method of locating a flaw position in a weld line of a material to be tested according to claim 1, said flaw data including echo height data and beam path length data, wherein when said echo height data lies within a predetermined voltage level range and when said beam path length data is not zero, said flaw data is sampled.

7. A method of locating a flaw position in a weld line of a material to be tested according to claim 1, wherein said probe position data is of the displacement along the X-axis, displacement along the Y-axis and angle of rotation of the $\Theta$-axis.

8. A method of locating a flaw position in a weld line of a material to be tested according to claim 1, wherein when differences between the probe position data and beam path length data sampled currently and the corresponding data sampled precedingly do not exceed associated predetermined values, respectively, and when the echo data sampled currently is of higher significance than the echo data sampled precedingly, only the currently sampled echo data is stored by replacing the echo data sampled precedingly.

* * * * *